(12) United States Patent
Liu et al.

(10) Patent No.: US 8,556,924 B2
(45) Date of Patent: Oct. 15, 2013

(54) NATURAL ORIFICE TRANSLUMENAL ENDOSCOPIC SURGERY (NOTES) DEVICE

(75) Inventors: Yun-Hen Liu, Guishan Shiang (TW); Ching-Yang Wu, Linkou Township, Taipei County (TW); Po-Jen Ko, Taipei (TW)

(73) Assignee: Chang Gung Medical Foundation, Linkou Branch, Taoyuan County (TW)

( * ) Notice: Subject to any disclaimer, the term of this patent is extended or adjusted under 35 U.S.C. 154(b) by 0 days.

(21) Appl. No.: 13/494,494

(22) Filed: Jun. 12, 2012

(65) Prior Publication Data

US 2012/0253376 A1 Oct. 4, 2012

Related U.S. Application Data

(63) Continuation-in-part of application No. 12/649,669, filed on Dec. 30, 2009, now abandoned.

(51) Int. Cl.
*A61B 17/34* (2006.01)
(52) U.S. Cl.
USPC ............................................. 606/185
(58) Field of Classification Search
USPC ......... 604/48, 93.01, 272, 276, 274; 606/185, 606/190, 191, 193, 197, 222; 600/184
See application file for complete search history.

(56) References Cited

U.S. PATENT DOCUMENTS

| | | | | |
|---|---|---|---|---|
| 5,064,411 A | * | 11/1991 | Gordon, III | 604/48 |
| 5,158,543 A | * | 10/1992 | Lazarus | 604/164.1 |
| 6,702,790 B1 | | 3/2004 | Ross et al. | |
| 6,916,330 B2 | * | 7/2005 | Simonson | 606/191 |
| 7,008,431 B2 | | 3/2006 | Simonson | |
| 7,641,659 B2 | * | 1/2010 | Emstad et al. | 606/86 R |
| 7,811,303 B2 | * | 10/2010 | Fallin et al. | 606/191 |
| 8,066,730 B2 | * | 11/2011 | Dorman | 606/191 |
| 2003/0083688 A1 | * | 5/2003 | Simonson | 606/191 |
| 2003/0083689 A1 | * | 5/2003 | Simonson | 606/191 |

* cited by examiner

*Primary Examiner* — Ryan Severson
*Assistant Examiner* — Jonathan W Miles (57) ABSTRACT

A natural orifice translumenal endoscopic surgery (NOTES) device is provided with a puncture needle including a puncture end, an intermediate protruding safety stud, and a positioning projection on an outer surface; dilator sheaths each including tapered first diameters, an insert member at one end, a limiting shoulder at the other end, a positioning protrusion on an outer surface, and a groove on an inner surface; working sheaths each having a plurality of tapered second diameters and including a positioning protuberance on an outer surface and a trough on an inner surface; and a tool member including a shaft having a graduation on an outer surface, and an operating head threadedly secured to the shaft.

4 Claims, 12 Drawing Sheets

NATURAL ORIFICE TRANSLUMENAL ENDOSCOPIC SURGERY (NOTES) DEVICE

CROSS-REFERENCED TO RELATED APPLICATIONS

This application is a Continuation-In-Part of application Ser. No. 12/649,669, filed Dec. 30, 2009, and this application claims priority from that application which is also deemed incorporated by reference in its entirety in this application.

STATEMENT REGARDING FEDERALLY SPONSORED RESEARCH OR DEVELOPMENT

Not applicable

FIELD OF THE INVENTION

The present invention generally relates to a technical field of surgical device, in particular, to a natural orifice translumenal endoscopic surgery (NOTES) device.

BACKGROUND OF THE INVENTION

At early stage, a surgical operation such as a thoracic surgery generally leaves a large wound and causes a serious postoperative pain to patients. As modern medicine and medical instruments have been advanced, minimal invasive surgery (MIS) has become a trend of current medical treatments. Along with the development of medical imaging equipments, endoscopic surgery has become a representative of minimal invasive surgery. The endoscopic surgery not only brings a revolutionary change to medical treatments only, but also reduces the post-operation pain to patients. Even so, the endoscopic surgery still needs to create several minor wounds on a patient's body in order to let an endoscopic device enter into the patient's body for the surgical operation. Therefore, the patient still has to bear with an acute postoperative pain and requires a follow-up treatment of possible wound scars. Obviously, such surgery has an adverse impact on the quality of life of the patients.

However, many imaging systems are used for entering the natural orifices of a patient's body for different medical treatments as the medical imaging equipments have been advanced. With the limitations of surgical devices and technologies, scarless surgical operations through natural orifices are still immature. In recent years, the technology of natural orifice translumenal endoscopic surgery (NOTES) has been developed rapidly, and different surgical operations can be performed with an endoscope passed through a natural orifice (such as an oral cavity, a colon cavity, and a birth channel) then through an internal incision into the body. The postoperative wound is reduced significantly, and a scarless operation can be achieved without affecting the patient's appearance and, thus, NOTES has many advantages over laparoscopy and thoracoscopy. However, NOTES requires more sophisticated surgical skills and only an experienced endoscopic surgery doctor to achieve a high success rate and safety.

The concept of the natural orifice translumenal endoscopic surgery was proposed in 2004. Current literatures related to the successful experience of animal experiments include abdominal and laparoscopic explorations plus liver section surgery, ovary and partial hysterectomy, gastrojejunostomy, tubal ligation, cholecysto-jejunostomy, cholecystectomy, abdominal lymphadenectomy, hernioplasty and proctocolectomy, etc. In 2005, surgical doctors first adopted the NOTES technology on human surgery for appendectomy, and then other NOTES surgeries taken place are laparoscopic exploration and cholecystectomy.

Popular subjects of the NOTES include: how to select an endoscopic entry, prevention of a postoperative infection, sewing-up a postoperative endoscopic entry, and design of endoscopic equipments. Among them, the design and development of the endoscope are the first step of the development of NOTES. Only the best design and user-friendly surgical machinery can provide a good foundation for the surgery and, thus, it is necessary to design appropriate surgical machinery for a specific natural orifice to achieve the effects of NOTES.

In view of the aforementioned shortcomings of the prior art, the inventor of the present invention based on years of experience in the related industry to conduct extensive researches and experiments, and finally developed a NOTES device in accordance with the present invention to overcome the shortcomings of the prior art.

SUMMARY OF THE INVENTION

It is a primary objective of the present invention to overcome the shortcomings of the prior art by providing a natural orifice translumenal endoscopic surgery (NOTES) device which comprises a puncture needle comprising a puncture end, a protruding safety stud disposed at a position substantially at a middle section of the puncture needle, and a positioning projection on an outer surface wherein the puncture needle is provided for puncturing into an internal wall of a nature lumen at the beginning of a surgical procedure; a plurality of dilator sheaths each comprising a plurality of tapered first diameters, an insert member at one end, and a limiting shoulder at the other end, each dilator sheath being sheathed sequentially onto the puncture needle and each dilator sheath further comprising an elongated positioning protrusion on an outer surface and an elongated groove on an inner surface, the groove being disposed correspondingly to the positioning protrusion wherein the positioning projection is complementarily received in the groove when the puncture needle is disposed in the dilator sheath, and the protruding safety stud of the puncture needle is stopped by the limiting shoulder such that such that the insert member is not allowed to pass through the puncture end; a plurality of working sheaths each having a plurality of tapered second diameters, and each of the tapered second diameters of the working sheaths being slightly greater than each of the tapered first diameters of the dilator sheaths wherein each of the working sheaths comprises an elongated positioning protuberance on an outer surface and an elongated trough on an inner surface, the trough being disposed correspondingly to the positioning protuberance, the positioning protrusion being complementarily received in the trough when the dilator sheath is disposed in the working sheath, and the working sheath being used for inserting and retracting the dilator sheaths and the puncture needle after the dilator sheaths have expanded a natural orifice; and a tool member comprising a cylindrical shaft including a graduation on an outer surface, and an operating head threadedly secured to one end of the cylindrical shaft.

The above and other objects, features and advantages of the invention will become apparent from the following detailed description taken with the accompanying drawings.

DETAILED DESCRIPTION OF THE PREFERRED EMBODIMENTS

Figure 1:
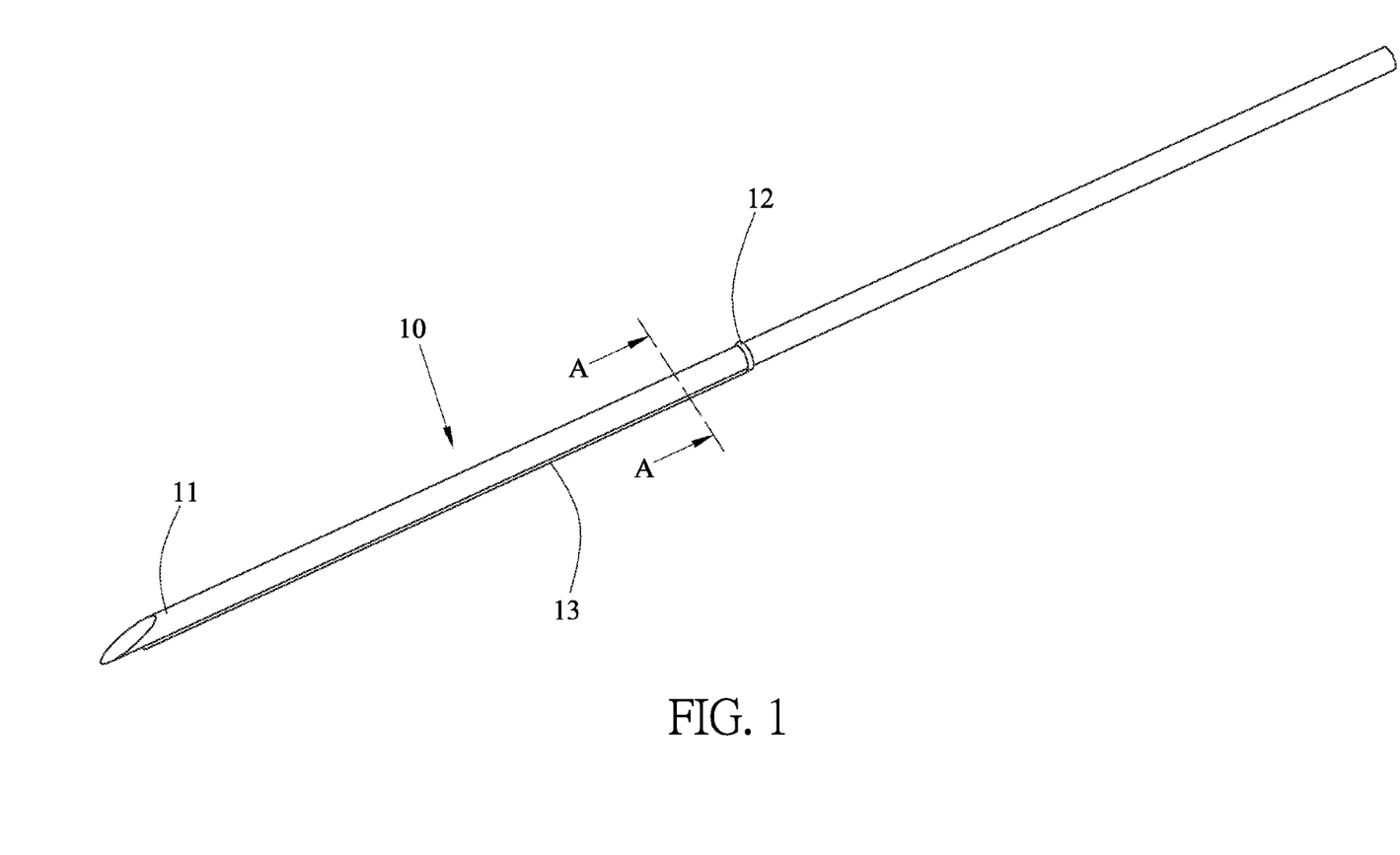
FIG. 1 is a perspective view of a puncture needle in accordance with a preferred embodiment of the present invention.
Figure 1A:
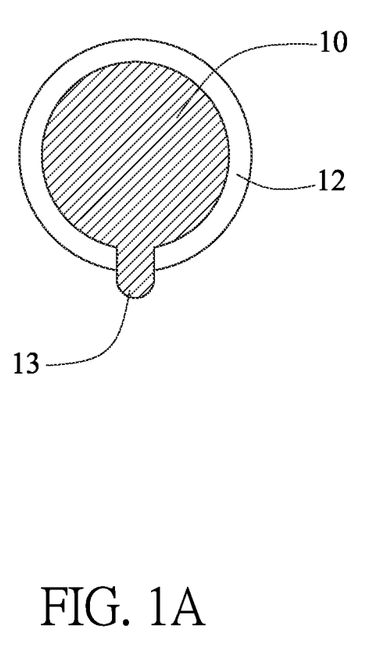
FIG. 1A is a sectional view taken along line A-A of FIG. 1.
Figure 2:
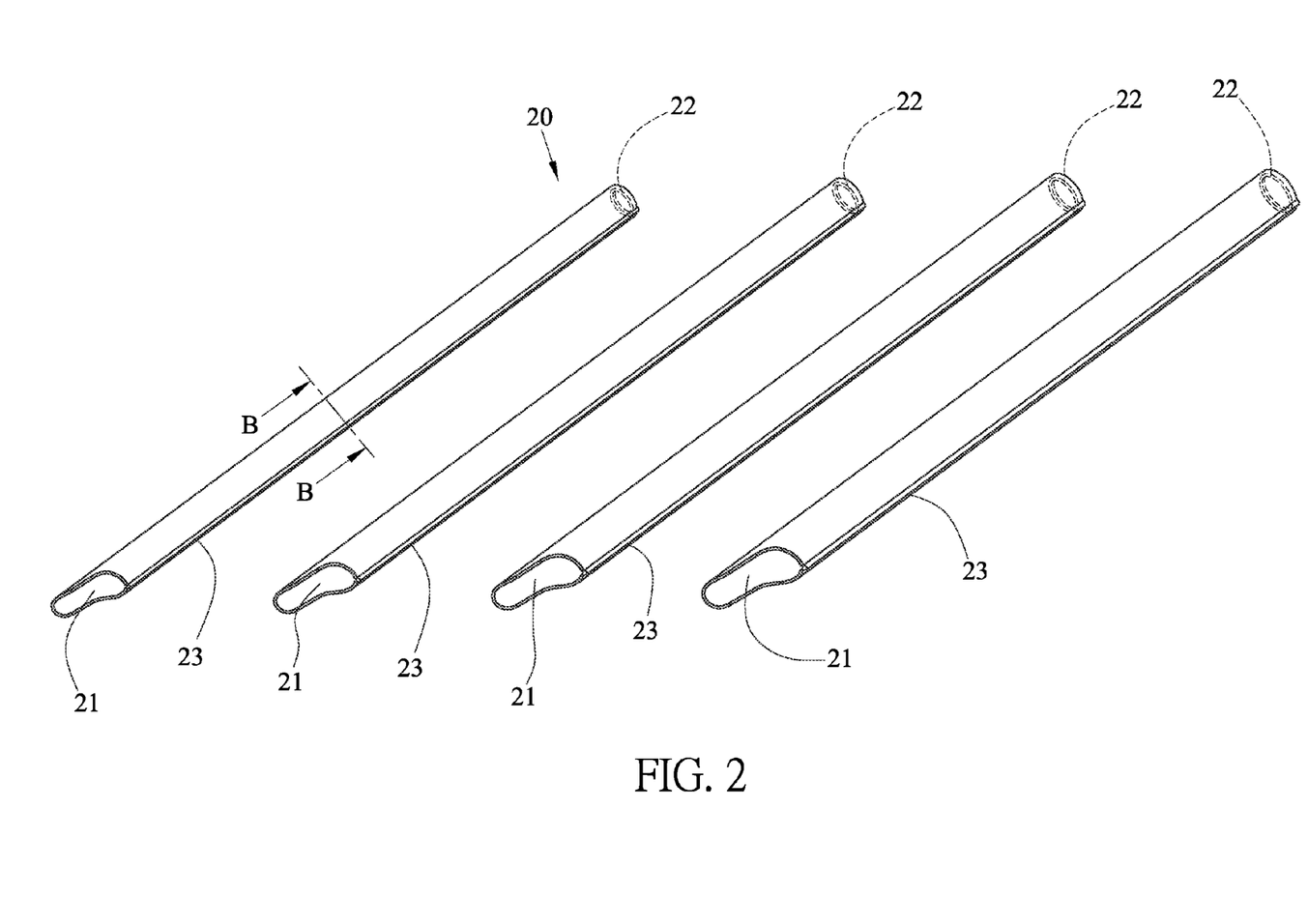
FIG. 2 is a perspective view of a dilator sheath in accordance with a preferred embodiment of the present invention.
Figure 2A:
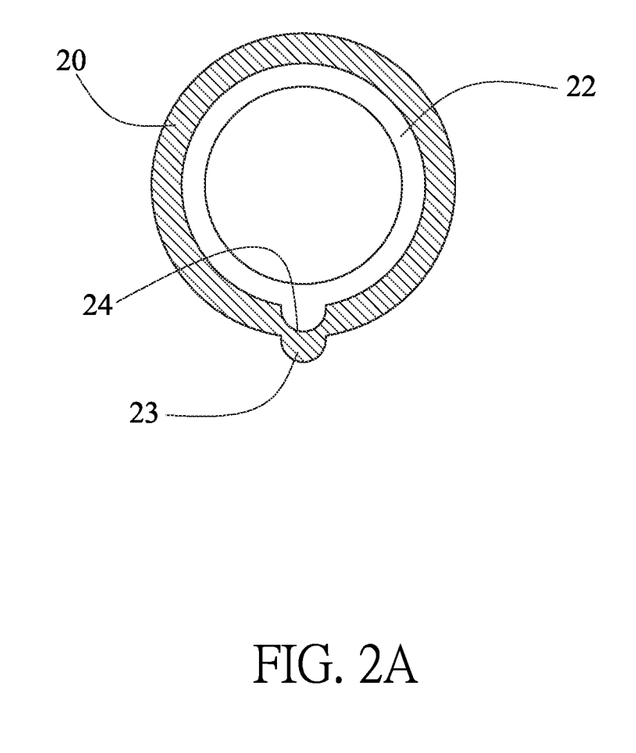
FIG. 2A is a sectional view taken along line B-B of FIG. 2.
Figure 3:
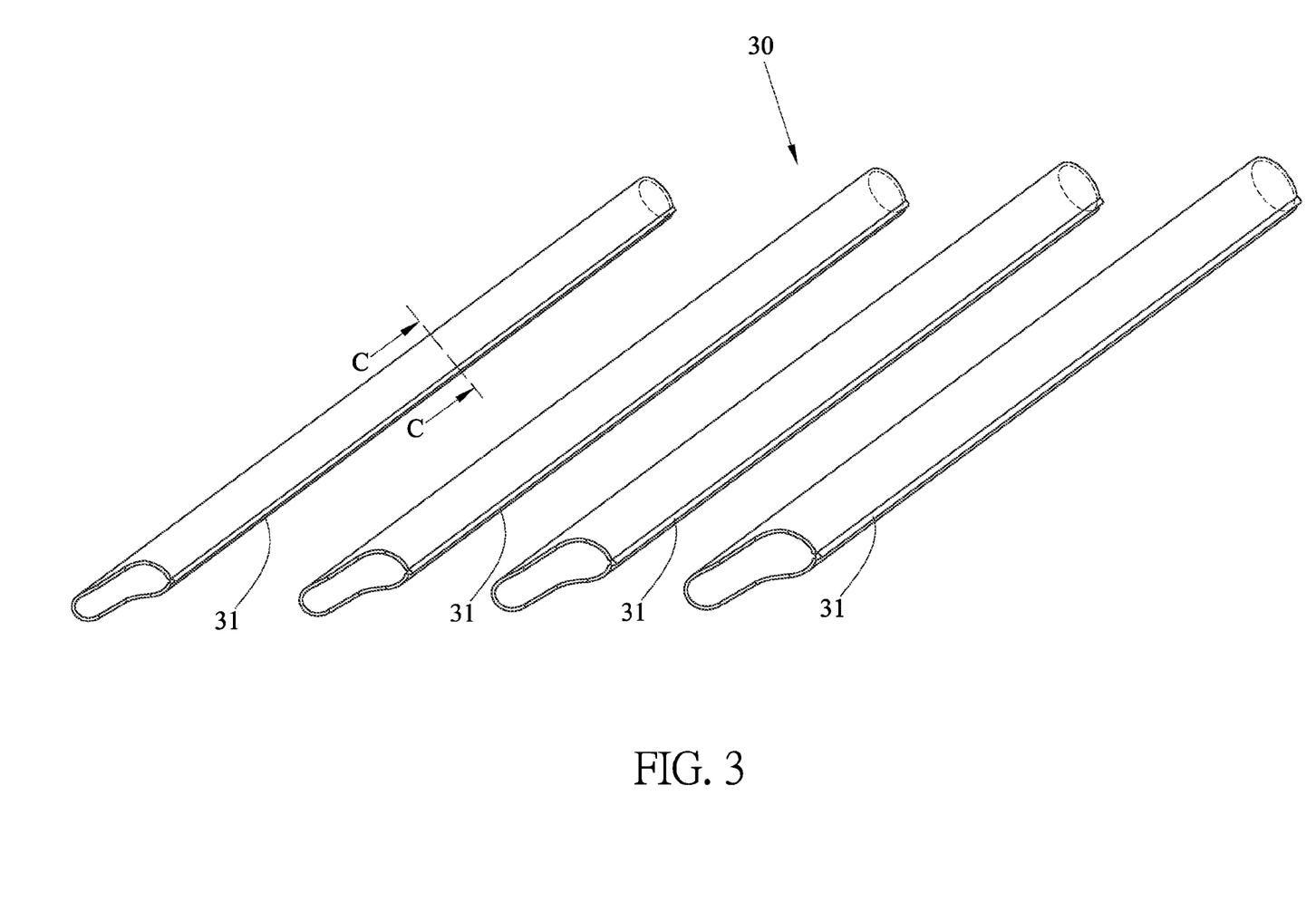
FIG. 3 is a perspective view of a working sheath in accordance with a preferred embodiment of the present invention.
Figure 3A:
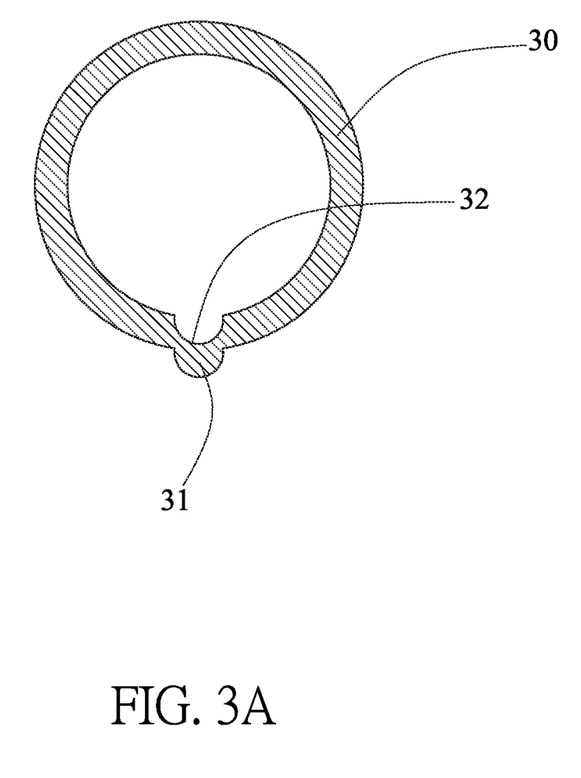
FIG. 3A is a sectional view taken along line C-C of FIG. 3.
Figure 4A:
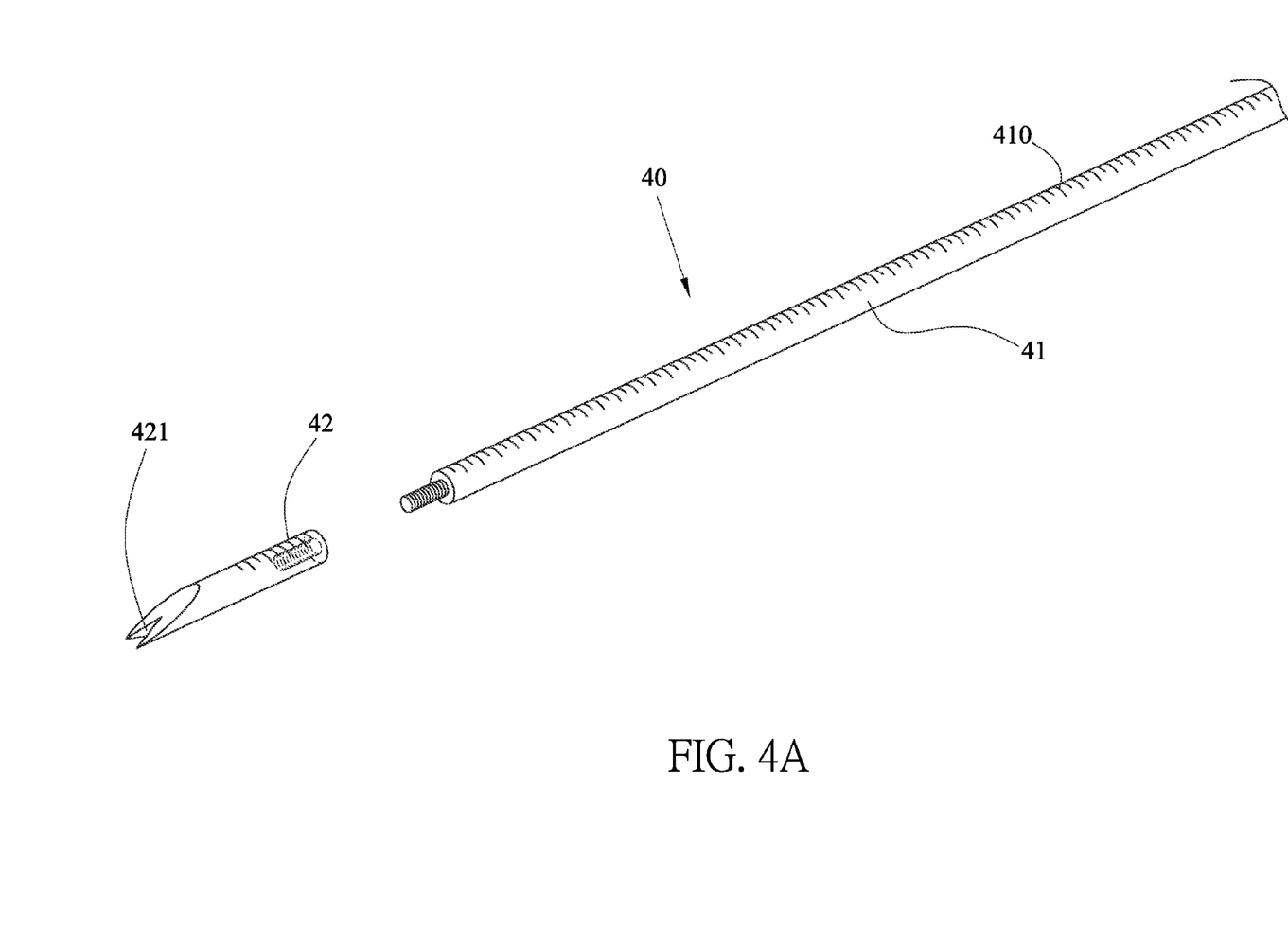
FIG. 4A is an exploded view of a tool member in accordance with a first configuration of the present invention.
Figure 4B:
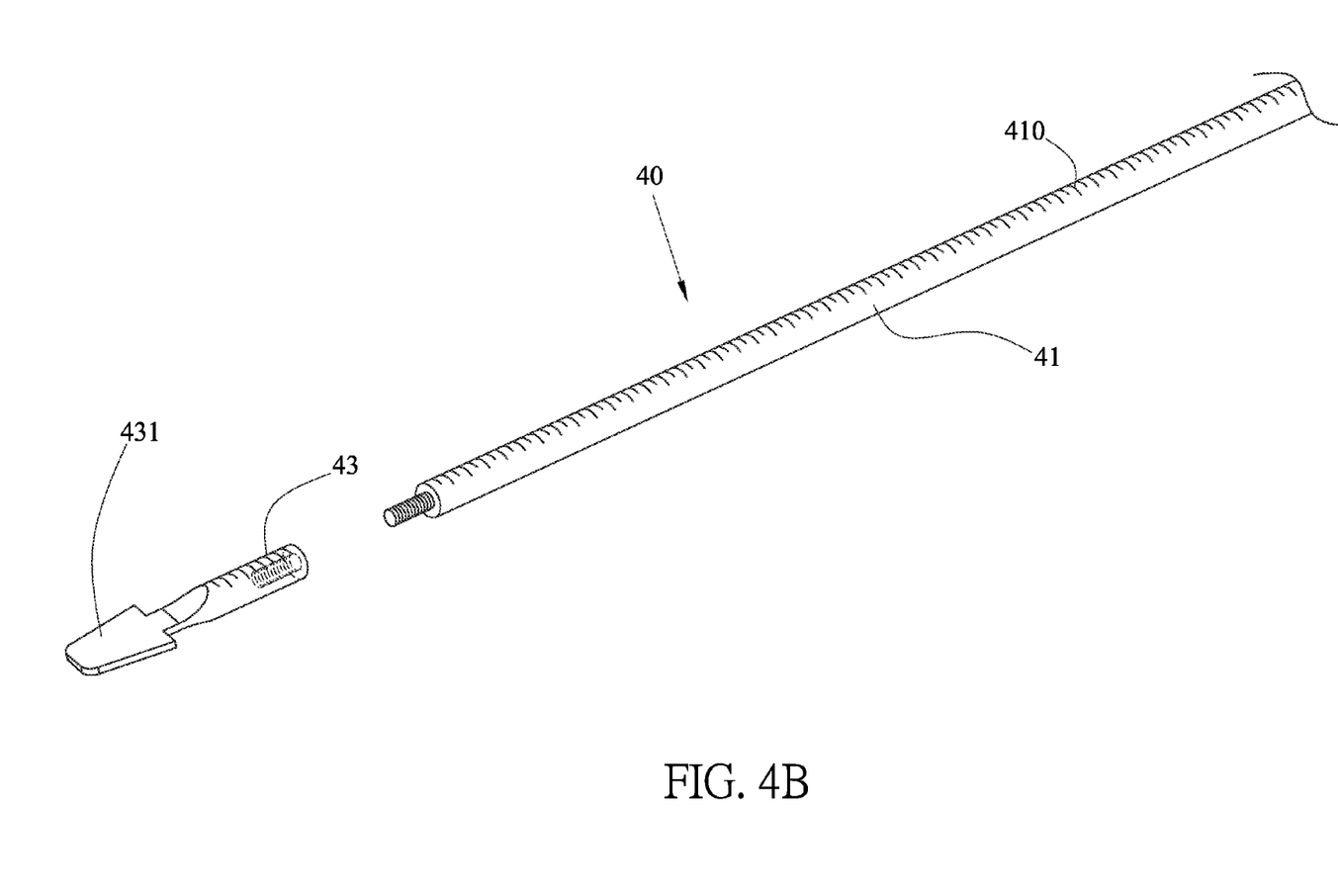
FIG. 4B is an exploded view of a tool member in accordance with a second configuration of the present invention.
Figure 4C:
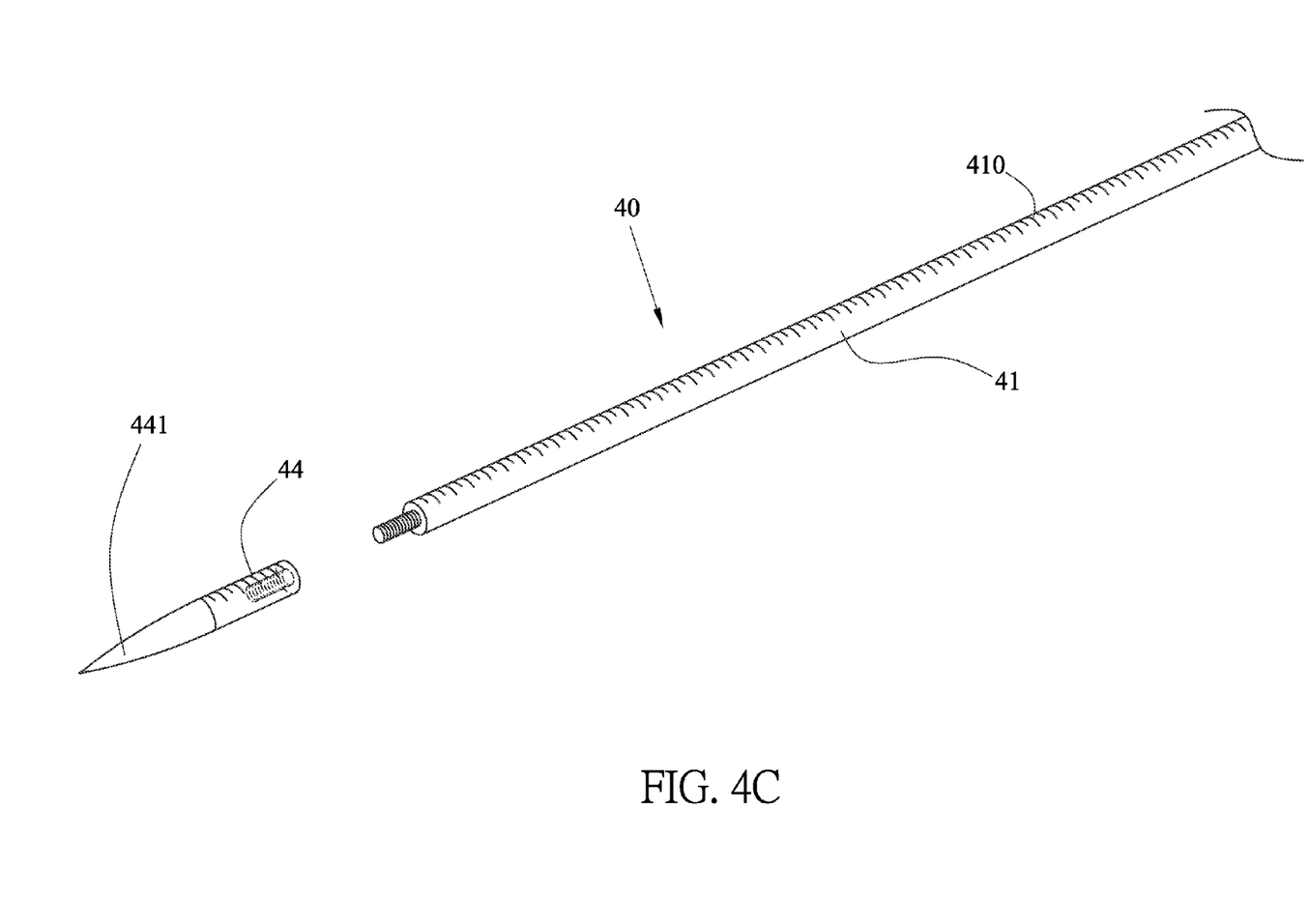
FIG. 4C is an exploded view of a tool member in accordance with a third configuration of the present invention.
Figure 5:
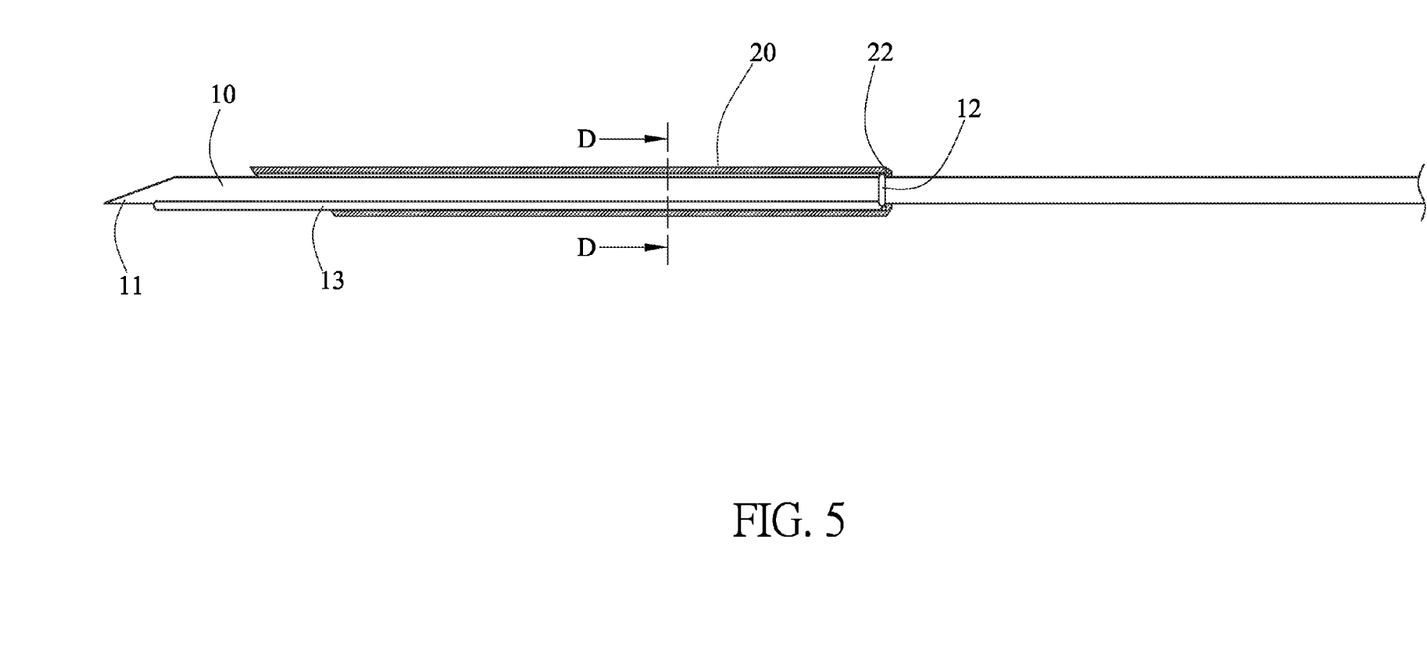
FIG. 5 is a side view of a puncture needle coupled to a dilator sheath in accordance with a preferred embodiment of the present invention.
Figure 5A:
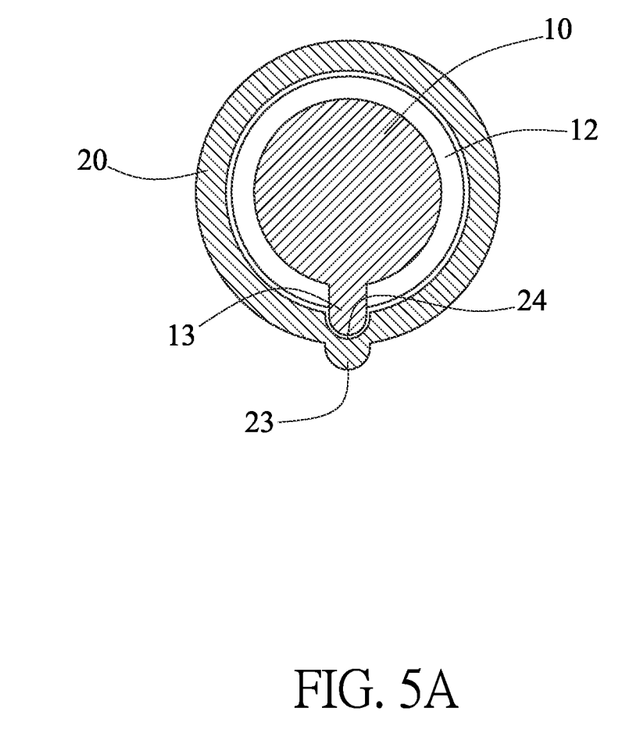
FIG. 5A is a sectional view taken along line D-D of FIG. 5.

With reference to FIGS. 1 to 6, a NOTES device of the present invention is shown. The device comprises a puncture needle 10, a plurality of dilator sheaths 20, a plurality of working sheaths 30, and a tool member 40. The puncture needle 10 comprises a puncture end 11, a protruding safety stud 12 disposed substantially at a position of a middle section of the puncture needle 10. The puncture needle 10 includes an elongated positioning projection 13 on an outer surface (FIG. 1). The puncture needle 10 is provided for puncturing into an internal wall of nature lumen at the beginning of the surgical procedure. The nature lumen wall can be a tracheal wall, or an internal wall of other natural orifices. In the present invention, an embodiment of the tracheal wall is used for the illustration. The dilator sheath 20 comprises a plurality of tapered first diameters (or a series of different successively increasing diameters), an insert member 21 at one end, and a limiting shoulder 22 at the other end opposite to the insert member 21. Each dilator sheath 20 is sheathed sequentially onto the puncture needle 10. Each dilator sheath 20 further includes an elongated positioning projection 23 on an outer surface and an elongated groove 24 on an inner surface, the groove 24 being disposed correspondingly to the positioning projection 23 (FIG. 2). The positioning projection 13 is partially, complementarily received in the groove 24 for guiding and positioning purposes when the puncture needle 10 is disposed in the dilator sheath 20 (FIG. 5). Thus, the dilator sheath 20 and the puncture needle 10 can be sequentially slid in place. Otherwise, tissues adjacent the bronchus may be damaged. The protruding safety stud 12 of the puncture needle 10 is stopped by the limiting shoulder 22 such that the insert member 21 will not exceed the puncture end 11 and will form a safety interval from the puncture end. The working sheaths 30 have a plurality of tapered second diameters (or a series of different successively increasing diameters), and each of the second diameters of the working sheaths 30 is slightly greater than each of the first diameters of the dilator sheaths 20.

The working sheath 30 comprises an elongated positioning projection 31 on an outer surface and an elongated groove 32 on an inner surface, the groove 32 being disposed correspondingly to the positioning projection 31 (FIG. 3). The positioning projection 23 is complementarily received in the groove 32 for guiding and positioning purposes when the dilator sheath 20 is disposed in the working sheath 30. The working sheath 30 is used for inserting and retracting the dilator sheaths 20 and the puncture needle 10 after the dilator sheaths 20 have expanded a natural orifice. Only the working sheath 30 is remained to form a space required for the surgical operation. Thus, the working sheath 30 can be correctly guided along the dilator sheath 20. In addition, a breathing apparatus can be connected when the working sheath 30 is used.

As shown in FIG. 4A, a first configuration of the tool member 40 comprises an elongated, cylindrical shaft 41 and a steel cutting needle 42 releasably secured to the shaft 41. The steel cutting needle 42 has an inclined surface with a V-shaped sharp end 421.

As shown in FIG. 4B, a second configuration of the tool member 40 comprises an elongated, cylindrical shaft 41 and a steel cutting needle 43 releasably secured to the shaft 41. The steel cutting needle 43 has a trapezoidal end 431

As shown in FIG. 4C, a third configuration of the tool member 40 comprises an elongated, cylindrical shaft 41 and a steel cutting needle 44 releasably secured to the shaft 41. The steel cutting needle 44 has a pointed end 441.

In each of the first to third configurations, an externally threaded extension is formed at one end of the shaft 41 and the other end of each of the steel cutting needles 42, 43 and 44 is provided with an externally threaded hole for threadedly securing to the externally threaded extension of the shaft 41. Moreover, the tool member 40 further comprises a graduation 410 on an outer surface for measuring the location of damaged tissues and allowing an appropriate surgical instrument to perform a surgical procedure.

The V-shaped sharp end 421 of the steel cutting needle 42 can be complimentarily disposed on an inclined surface for embedding and cutting a surgical thread at the end of the surgical procedure. Further, the trapezoidal end 431 of another steel cutting needle 43 is used for outward deflecting the tissues in a surgical procedure. It is a physician's choice of using one of the three steel cutting needles 42, 43 and 44 in surgical procedure.

The puncture needle 10 has a first length substantially equal to 70 cm.

The dilator sheath 20 has a second length substantially equal to 33 cm. The safety interval is substantially equal to 2 cm.

The plurality of first diameters can be equal to 5 mm, 7 mm, 9 mm and 11 mm respectively. In other words, the dilator sheaths 20 have diameters equal to 5 mm, 7 mm, 9 mm, and 11 mm sequentially for expanding an orifice.

The plurality of second diameters can be equal to 7 mm, 9 mm, 11 mm, and 13 mm respectively. In other words, the plurality of working sheaths 30 can have diameters of 7 mm, 9 mm, 11 mm, and 13 mm respectively for maintaining the smoothness of the orifice during the operation.

Figure 6:
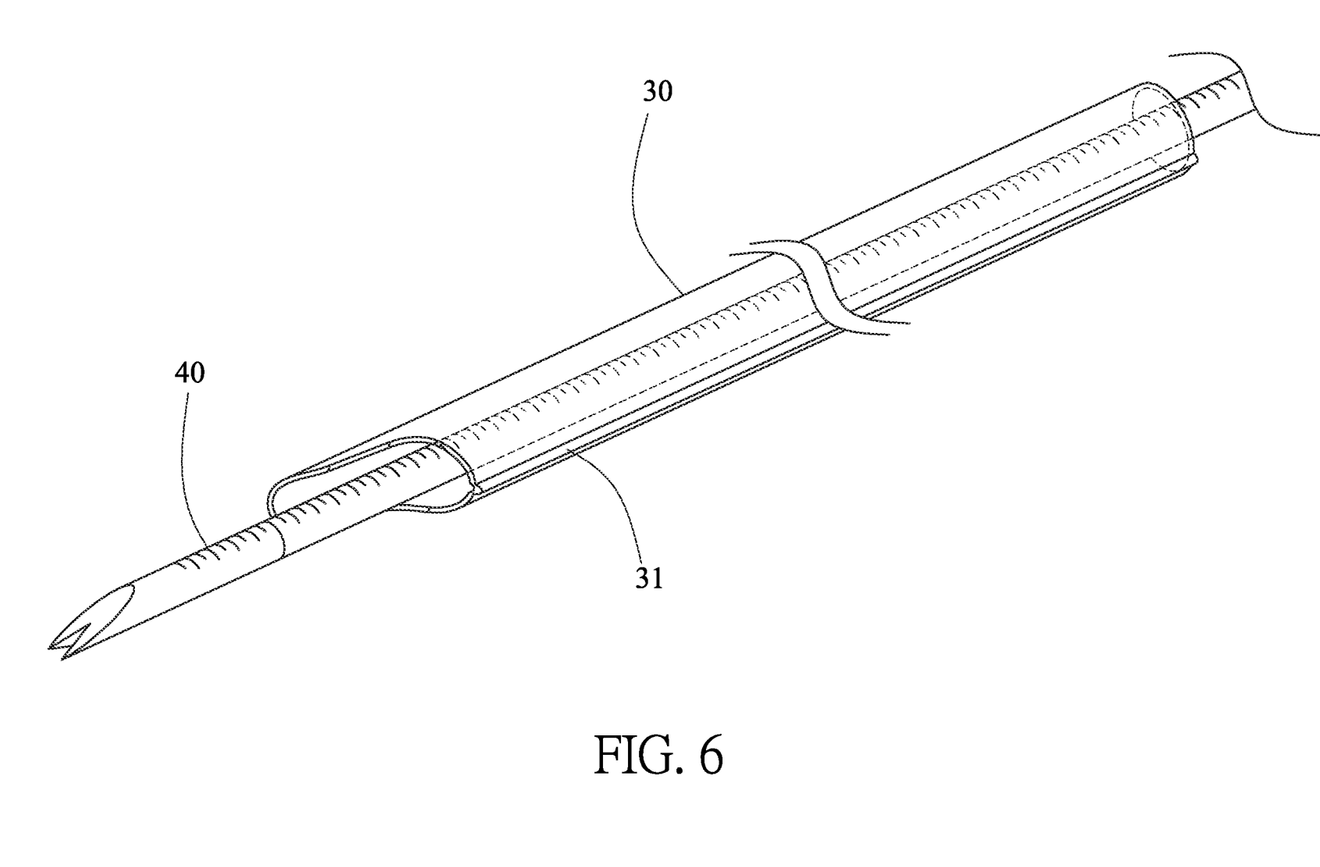
FIG. 6 is a perspective view showing the tool member passing through the working sheath in a surgical procedure.

In general, the endoscope is entered from a trachea during a surgical operation, and a rigid (or soft) bronchoscopy is used for the surgical operation, and then the puncture needle 10 is inserted into the trachea, and the plurality of dilator sheaths 20 expand an orifice, and a working sheath 30 is used for maintaining the smoothness of the orifice during the surgical operation, and then a rigid bronchoscopy machinery (a rigid one has been used clinically) is used for a surgical operation, and the tool member also is disposed in the working sheath 30 in the surgical operation (FIG. 6).

In addition, a method or procedure of the present invention comprises the steps of (a) creating a stable airway by a rigid bronchoscopy; (b) selecting an appropriate puncture position; (c) passing a surgical sheath from a tracheal sidewall situated at a position substantially 3 cm from the top of a tracheal carina and out of a trachea through a natural orifice; (c1) passing a puncture needle 10 out of the tracheal sidewall; (c2) passing a series of dilator sheaths 20 with tapered diameters along the puncture needle 10 sequentially to create an opening; (c3) preventing unnecessary damages by a design of a safety stud 12 which latches the dilator sheath 20 at a position substantially 2 cm from the tip of the puncture needle 10; (c4) expanding the opening sequentially, and then retracting the dilator sheath 20 to a position of a sheath with one size smaller than the desired working sheath 30; (c5) passing the working sheath 30 through the puncture needle 10 and the opening into a pleural space; (d) using the rigid bronchoscopy machinery for the surgical operation after creating a working channel; (d1) exchanging air by the working sheath 30 of the rigid bronchoscopy during the surgical operation; (d2) prohibiting a removal of the sheath during the surgical operation; (e) making sure that the oxygen level of an experimental animal or a patient reaches 100% before removing the working sheath 30; (f) removing the working sheath 30 after the air exchange is terminated; (g) immediately installing a tracheal stent after the working sheath 30 is removed; (g1) selecting the tracheal stent primarily by using a silicone stent (which can be removed easily), and evaluating the tracheal stent by a 3D CT before the surgical operation takes place; (g2) covering the opening of the trachea to avoid a pneumothorax; (g3) performing the endoscopic examination to confirm the position of the stent after the tracheal stent is disposed, wherein if the wound is smaller than one-third of the external circumference of the trachea, then the trachea will be healed automatically; and (h) performing a rigid bronchoscopic examination after the surgical operation takes place, and performing a stent removal operation if the incision healing condition is good. In general, the tracheal stent is covered onto a wound orifice, and the tracheal stent can be removed after two weeks when the wound has been recovered naturally.

In brief, the present invention provides a NOTES device that is disposed in a trachea to achieve the advantages of the NOTES, and the design of the device provides a user-friendly and easy operation for a scarless surgical operation without affecting a patient's appearance. In addition, the present invention further includes a protruding safety stud disposed at a position substantially at a middle section of the puncture needle, such that the dilator sheath can be latched at a position substantially 2 cm from the tip of the puncture needle to prevent unnecessary damages.

While the invention has been described in terms of preferred embodiments, those skilled in the art will recognize that the invention can be practiced with modifications within the spirit and scope of the appended claims.

What is claimed is:

1. A natural orifice translumenal endoscopic surgery (NOTES) system, comprising:
    a puncture needle comprising a puncture end, a protruding safety stud disposed at a position substantially at a middle section of the puncture needle, and a positioning projection on an outer surface wherein the puncture needle is provided for puncturing into an internal wall of a nature lumen at the beginning of a surgical procedure;
    a plurality of dilator sheaths each comprising a plurality of tapered first diameters, an insert member at one end, and a limiting shoulder at the other end, each dilator sheath being sheathed sequentially onto the puncture needle and each dilator sheath further comprising an elongated positioning protrusion on an outer surface and an elongated groove on an inner surface, the groove being disposed correspondingly to the positioning protrusion wherein the positioning projection is complementarily received in the groove when the puncture needle is disposed in the dilator sheath, and the protruding safety stud of the puncture needle is stopped by the limiting shoulder such that such that the insert member is not allowed to pass through the puncture end;
    a plurality of working sheaths each having a plurality of tapered second diameters, and each of the tapered second diameters of the working sheaths being slightly greater than each of the tapered first diameters of the dilator sheaths wherein each of the working sheaths comprises an elongated positioning protuberance on an outer surface and an elongated trough on an inner surface, the trough being disposed correspondingly to the positioning protuberance, the positioning protrusion being complementarily received in the trough when the dilator sheath is disposed in the working sheath, and the working sheath being used for inserting and retracting the dilator sheaths and the puncture needle after the dilator sheaths have expanded a natural orifice; and
    a tool member comprising a cylindrical shaft including a graduation on an outer surface, and an operating head threadedly secured to one end of the cylindrical shaft.

2. The NOTES system of claim 1, wherein the operating head is an inclined surface having a V-shaped sharp end.

3. The NOTES system of claim 1, wherein the operating head is trapezoidal.

4. The NOTES system of claim 1, wherein the operating head is pointed.

* * * * *